(12) United States Patent
Vinayagamoorthy

(10) Patent No.: US 8,785,130 B2
(45) Date of Patent: Jul. 22, 2014

(54) USE OF MARKERS INCLUDING NUCLEOTIDE SEQUENCE BASED CODES TO MONITOR METHODS OF DETECTION AND IDENTIFICATION OF GENETIC MATERIAL

(75) Inventor: Thuraiayah Vinayagamoorthy, Saskatoon (CA)

(73) Assignee: Bio-Id Diagnostic Inc., Saskatchewan (CA)

( * ) Notice: Subject to any disclaimer, the term of this patent is extended or adjusted under 35 U.S.C. 154(b) by 0 days.

(21) Appl. No.: 11/481,046

(22) Filed: Jul. 6, 2006

(65) Prior Publication Data
US 2007/0072212 A1 Mar. 29, 2007

Related U.S. Application Data

(60) Provisional application No. 60/696,824, filed on Jul. 7, 2005.

(51) Int. Cl.
*C12Q 1/68* (2006.01)
*G06F 19/00* (2011.01)

(52) U.S. Cl.
USPC .......................................... 435/6.12; 702/20

(58) Field of Classification Search
None
See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 4,775,619 A | 10/1988 | Urdea | |
| 4,851,331 A | 7/1989 | Vary | |
| 4,965,188 A | 10/1990 | Mullis | |
| 5,227,292 A | 7/1993 | White et al. | |
| 5,376,355 A | 12/1994 | Turteltaub | |
| 5,403,707 A | 4/1995 | Atwood | |
| 5,451,505 A * | 9/1995 | Dollinger ..................... | 435/6.11 |
| 5,552,283 A | 9/1996 | Diamandis | |
| 5,582,989 A | 12/1996 | Caskey | |
| 5,622,824 A | 4/1997 | Koster | |
| 5,661,028 A | 8/1997 | Foote | |
| 5,711,310 A | 1/1998 | Vinayagamoorthy | |

(Continued)

FOREIGN PATENT DOCUMENTS

| | | |
|---|---|---|
| EP | 0318341 | 5/1989 |
| EP | 0208418 | 12/1998 |

(Continued)

OTHER PUBLICATIONS van Rooijen et al., Structural-Requirements of Oleosin Domains for Subcellular Targeting to the Oil Body, Plant Physiol. (1995) 109: 1353-1 361.*

(Continued)

*Primary Examiner* — Angela M Bertagna
*Assistant Examiner* — Danna Bicknell
(74) *Attorney, Agent, or Firm* — Morrison & Foerster LLP

(57) ABSTRACT

Disclosed is the use of artificially-generated nucleic acid coded markers to monitor nucleic acid amplification and sequencing reactions designed to detect or analyze biological samples. The markers generally include, along with a unique sequence preferably including coded section designed to represent one or more factors of interest, primer annealing sequences so that the marker may be amplified and sequenced in the same process and using the same amplification and sequencing primers as for the sample target. The invention also relates to the marker itself, and other uses, such as identifying the origin of various materials or products.

10 Claims, 8 Drawing Sheets

(56) References Cited

U.S. PATENT DOCUMENTS

| | | | |
|---|---|---|---|
| 5,776,737 | A | 7/1998 | Dunn |
| 5,912,129 | A | 6/1999 | Vinayagamoorthy |
| 5,994,528 | A | 11/1999 | Vinayagamoorthy |
| 6,010,908 | A | 1/2000 | Gruenert et al. |
| 6,030,657 | A * | 2/2000 | Butland et al. ............... 427/7 |
| 6,140,110 | A | 10/2000 | Vinayagamoorthy |
| 6,197,510 | B1 | 3/2001 | Vinayagamoorthy |
| 6,998,473 | B1 | 2/2006 | Crofts et al. |
| 2003/0165868 | A1* | 9/2003 | Lacroix ............... 435/6 |
| 2007/0072212 | A1 | 3/2007 | Vinayagamoorthy |
| 2008/0118915 | A1 | 5/2008 | Vinayagamoorthy |

FOREIGN PATENT DOCUMENTS

| | | | |
|---|---|---|---|
| WO | WO9104270 | 4/1991 | |
| WO | WO9113993 | 9/1991 | |
| WO | WO9119816 | 12/1991 | |
| WO | WO9306243 | 4/1993 | |
| WO | WO9410315 | 5/1994 | |
| WO | WO9421822 | 9/1994 | |
| WO | WO9511294 | 4/1995 | |
| WO | WO9743441 | 11/1997 | |
| WO | WO9826095 | 6/1998 | |
| WO | WO9929900 | 6/1999 | |
| WO | WO0020628 | 4/2000 | |
| WO | WO 00/66768 | * 11/2000 | ............... C12Q 1/68 |
| WO | WO2007095723 | 8/2007 | |
| WO | PCT/CA2007/002333 | 8/2008 | |

OTHER PUBLICATIONS

Sullivan et al., Identification of human remains by amplification and automated sequencing of mitochondrial DNA, Int J Leg Med (1992) 105 : 83-86.*

Cone et al., Coamplified Positive Control Detects Inhibition of Polymerase Chain Reactions,Journal of Clinical MICROBIoLOcY, Dec. 1992, p. 3185-3189, vol. 30, No. 12.*

Verdin et al., Use of an internal control in a nested-PCR assay for Mycoplasma hyopneumoniae detection and quantification in tracheobronchiolar washings from pigs, Molecular and Cellular Probes (2000) 14, 365-372.*

Reiter et al, Human Meiotic Recombination Products Revealed by Sequencing a Hotspot for Homologous Strand Exchange in Multiple HNPP Deletion Patients, Am. J. Hum. Genet. 62:1023-1033, 1998.*

Yang et al., Hypersensitive PCR, ancient human mtDNA, and contamination, Human Biology, vol. 75, pp. 355-364, 2003, pages printed as 1-6.*

Ehmer et al., Variation of Hepatic Glucuronidation: Novel Functional Polymorphisms of the UDP-Glucuronosyltransferase UGT1A4, Hepatology, vol. 39, No. 4, 2004, pp. 970-977, published online Mar. 25, 2004.*

Drosten et al., TaqMan 5'-Nuclease Human Immunodeficiency Virus Type 1 PCR Assay with Phage-Packaged Competitive Internal Control for High-Throughput Blood Donor Screening, Journal of Clinical Microbiology, Dec. 2001, p. 4302-4308.*

Gibson et al. A novel method for real time quantitative RT-PCR. Genome Res. 1996;6:995-1001.*

Yamakawa and Ohara, "A DNA Cycle Sequencing Reaction that Minimizes Compressions on Automated Fluorescent Sequencers", Nucleic Acid Research, vol. 25, No. 6, pp. 1131-1312.

van Doornum et al., 2003, "Diagnosing herpes virus infections by real-time amplification and rapid culture", Journal of Clinical Microbiology, vol. 41, pp. 576-580.

Akduman et al., 2002, "Evaluation of a strand displacement amplification assay (BD ProbeTec-SDA) for detection of *Neisseria gonorrhea* in urine specimens", Journal of Clinical Microbiology, vol. 40, pp. 281-283.

Roth et al., 1999, "Feasibility and efficacy of routine PCR screening of blood donations for hepatitis C virus, hepatitis B virus, and HIV-1 in a blood-bank setting", *Lancet*, vol. 353(9150), pp. 359-363.

Betsou et al., 2003, "Construction and evaluation of internal control Nucleic Acids for PCR amplification of *Chlamydia trachomatis* Nucleic Acids from urine samples", Journal of Clinical Microbiology, vol. 41, pp. 1274-1276.

Dingle et al., 2004, "Stable and noncompetitive RNA internal control for routine clinical diagnostic reverse transcription-PCR", Journal of Clinical Microbiology, vol. 42, pp. 1003-1011.

Gonzalez et al., 2005, "Multiple displacement amplification as a pre-polymerase chain reaction (pre-PCR) to process difficult to amplify samples and low copy number sequences from natural environments", Environ Microbiol., vol. 7, No. 7, p. 1024-1028.

Abu Al-Soud and Radstrom, 2000, "Effects of amplification facilitators on diagnostic PCR in the presence of blood, feces, and meat", Journal of Clinical Microbiology, vol. 38, No. 12, pp. 4463-4470.

Vinayagamoorthy et al., 2003, "Nucleotide sequence based multitarget identification", MultiGEN, Journal of Clinical Microbiology, pp. 3284-3292.

Schmittgen, T.D., Teske, S., Vessella, R.L., True, L.D., and Zakrajsek, B.A., Expression of prostate specific membrane antigen and three alternatively spliced variants of PSMA in prostate cancer patients, Int J Cancer, Nov. 1, 2003:107(2):323-9.

Bourdon J.C., et al., p53 isoforms can regulate p53 transcriptional activity, Aug. 30, 2005 Genes and Development 19(18):2122-37.

Fitch J.M., et al., Analysis of transcriptional isoforms of collagen types IX, II, and I in the developing avian cornea by competitive polymerase chain reaction (Jan. 1995) Developmental Dynamics 202(1):42-53.

Orban Ti et al., Expression profiles of BRCA1 splice variants in asynchronous and in G1/S synchronized tumor cell lines (Jan. 12, 2001) Biochemical and Biophysical Research Communications, 280(1):32-38.

Cross N., Detection of BCR-ABL in hematological malignancies by RT-PCR (1996) Methods in Molecular Medicine, Molecular Diagnosis of Cancer pp. 25-36.

Li et al., "Direct electrophoretic detection of the allelic states of single DNA molecules in human sperm by using the polymerase chain reaction" Proc. Natl. Acad. Sci USA vol. 87, pp. 4580-4584, 1990.

Rawn, "Biochemistry" pp. 666, 708, Carolina Biological Supply, North Carolina 1989.

S.C. Roemer et al., Simultaneous Bi-Directional Cycle Sequencing, LI-COR Virtual Poster Session [on-line], Sep. 1997, retrieed on Sep. 4, 1998, from Internet: <URL:http://www.licor.com/bio/Posters/GenSeq97/GenSeq97.htm>.

D.L. Steffens et al., Multiplex Amplification of Human STR Loci using Infrared Fluorescence Detection, LI-COR Virtual Poster Session [on-line], Feb. 1997.

Visible Genetics, Inc., Application Note, HiV Genotyping using the OpenGene Automated DNA Sequencing System, Jan. 16, 1998.

Visible Genetics, Inc., Application Note, p53 Mutation Detection using the OpenGene Automated DNA Sequencing System, May 3, 1998.

Jones, Leslie B. et al.: "Octamer-primed cycle sequencing using dye-terminator, chemistry" Nucleic Acids Research, vol. 26, No. 11, 1998, pp. 2824-2426, XP002131455.

Horton, Joseph H.: "Optimized Conditions for Cycle Sequencing of PCR Products" PCR Methods and Applications, vol. 3, 1994, pp. 359-360, XP002131456.

White, Michael J. et al.: "Concatemer Chain Reaction: A Taq DNA Polymerase-Mediated Mechanism for Generating Long Tandemly Repetitive DNA Sequences" Analytical Biochemistry, US, Academic Press, San Diego, CA, vol. 199, No. 2, Dec. 1, 1991, pp. 184-190, XP000236491.

Kretz, Keith et al.: "Cycle Sequencing" PCR Methods & Applications, US, Cold Spring Harbor Laboratory Press, vol. 3, No. 5, Apr. 1, 1994, pp. S107-S112, XP000606764.

Sanger, F. et al.: "DNA Sequencing with Chain-Terminating Inhibitors" Proceedings of the National Academy of Sciences of the USA, US, New York, NY, vol. 74, No. 12, Dec. 1, 1977, pp. 5463-5467, XP000603873.

Marechal et al. (2001) Hum Genet 108:290-298.

Johnson et al. (2003) Science vol. 302:2141-2144.

(56) References Cited

OTHER PUBLICATIONS

Kotera, J., Fujishige, K., Michibata, H., Yuasa, K., Kubo, A., Nakamura, Y., and Omori, K., Characterization and effects of methyl-2-(4-aminophenyl)-1, 2-dihydro-1-oxo-7-(2-pyridinylmethoxy)-4-(3,4,5-trimethoxyhenyl)-3-isoquinoline carboxylate sulfate (T-1032), a novel potent inhibitor of cGMP-binding cGMP-specific phosphodiesterase (PDE5), Biochem.Pharmacol., Nov. 1, 2000:60(9):1331-41.

Martin, M.M., Willardson, B.M., Burton, G.F., White, C.R., McLaughlin, J.N., Bray, S.M., Ogilvie, J.W. Jr., and Elton, T.S., Human angiotensin II type 1 receptor isoforms encoded by messenger RNA splice variants are functionally distinct, Mol. Endocrinol., Feb. 2001:15(2):281-93.

He, X., EE, P.L., Coon, J.S., and Beck, W.T., Alternative splicing of the multidrug resistance protein 1/ATP binding cassette transporter subfamily gene in ovarian cancer creates functional splice variants and is associated with increased expression of the splicing factors PTB and SRp20. Clin. Cancer Research, Jul. 15, 2004:10(14):4652-60.

Wharton, J., et al., Antiproliferative effects of phosphodiesterase type 5 inhibition in human pulmonary artery cells, American J. Respir Critt Care Med. Epub, Apr. 7, 2005:Jul. 1, 2005:172(1):105-13.

Molecular Typing of West Nile Virus, Dengue, and St. Louis Encephalitis Using Mutiplex Sequencing; Journal of Molecular Diagnostics; Moorthy, et al.; vol. 7, No. 2, May 2005.

DNA Sequence-Based High-Throughout Microbial Identification Using Multiplex Sequencing; Moorthy; American Biotechnology Laboratory, Dec. 2003.

Detection of *Giardia lamblia* and *Cryptosporidium parvum* in Water Samples Using Multiplex Sequencing Technology; Moorthy; American Laboratory, May 2004.

Rational Drug Design Based on Splice Variants; Moorthy; GEN vol. 24, No. 9, May 1, 2004.

Polymicrobial Disease Conference Chart: Identification of West Nile and Other Flaviviruses Using Multiplex Sequencing (MultiGEN), Oct. 19-23, 2003, Lake Tahoe.

Human Meiotic Recombination Products Revealed by Sequencing a Hotspot for Homologous Strand Exchange in Multiple HNPP Deletion Patients; Reiter, et al.; Am. J. Hum. Genet. 62:1023-1033, 1998.

Hypersensitive PCR, Ancient Human mtDNA, and Contamination; Yang; Human Biology, vol. 75, pp. 355-364, 2003.

Identifying MRSA with Multiplex Sequencing; Moorthy, et al.; GEN vol. 28, No. 6, Mar. 15, 2008.

Molecular cloning, sequencing, and analysis of the cDNA for rabbit muscle glycogen debranching enzyme, Vinayagamoorthy, et al. Archives of Biochemistry and Biophysics 1993 vol. 306 No. 1 pp. 232-239.

Molecular control of melanogenesis in malignant melanoma: functional assessment of tyrosinase and lamp gene families by UV exposure and gene co-transfection, and cloning of a cDNA encoding calnexin, a possible melanogenesis "chaperone", Vinayagamoorthy, et al. J Dermatol Nov. 1994; 21(11):894-906.

Novel type of plasmid-borne resistance to trimethoprim, Vinayagamoorthy, et al. Antimicrob Agents Chemother Jan. 1987; 31(1):60-66.

Identification of a cDNA coding for a Ca(2+)-binding phosphoprotein (p90), calnexin, on melanosomes in normal and malignant human melanocytes, Vinayagamoorthy et al. Exp Cell Res Dec. 1993; 209(2):288-300.

Characterization of melanosome-associated proteins by establishment of monoclonal antibodies and immunoscreening of a melanoma cDNA library through an anti-melanosome antibody, Vinayagamoorthy et al. Melanoma Res. Oct. 1993;3(5):331-6.

Research Report, A rapid non-selective method to generate quadromas by microelectrofusion. Vinayagamoorthy, et al. doi:10.1016/0022-1759(95)00160-C.

cDNA-based functional domains of a calnexin-like melanosomal protein, p90. Vinayagamoorthy et al. Melanoma Res. Aug. 1993;3(4):263-9.

Stress Relief Protein Modulation by Calnexin. Vinayagamoorthy et al. Annals of the New York Academy of Sciences, 1996.

Simultaneous genotyping of sexually transmitted bacterial pathogens using MultiGEN technology. Vinayagamoorthy et al. International Society for Sexually Transmitted Diseases.

Incidence of pGS01 and pGSO4 type sulphonamide resistance genes among clinical isolates collected from hospitals in Sri Lanka. Vinayagamoorthy et al. Singapore Med J. Aug. 1986;27(4):312-6.

Identification of Food Pathogens Using Multiple Nucleotide Based Signature Sequences. Presentation apart of PS 6C: Biotechnology Applications. Vinayagamoorthy et al. Friday, Jul. 18, 2003.

Identification of the Severe Acute Respiratory Syndrome Coronavirus by Simultaneous Multigene DNA Sequencing. Vinayagamoorthy et al. Journal of Clinical Microbiology, Jul. 2004, p. 3291-3294, vol. 42, No. 7.

24 hour urine composition of Sri Lankan adults and their response to 100mg dihydrochlorothiazide. Vinayagamoorthy et al. Ann Clin Biochem Jul. 1980;17(4):212-3.

Mobilization of antibiotic resistance genes among farm animals and human hosts in a developing country (Sri Lanka). Vinayagamoorthy et al. Singapore Medical Journal 1987 vol. 28 No. 2 pp. 134-139.

R-plasmid-mediated antibiotic resistance genes among clinical isolates, "normal healthy" adults and a drinking water source in a developing country. Vinayagamoorthy et al. Asian Medical Journal vol. 29, No. 1, pp. 50-68 1986.

"Dual asymetric PCR: one-step construction of synthetic genes" Sandhu, G.S., et al. BioTechnics vol. 12, No. 1, Jan. 1992 pp. 14-16.

Gene synthesis and expression in *E. coli* for PMP, a human matrix metalloproteinase Ye, Q-Z, et al. Biochemical and Biophysical Research Communications vol. 186, Jul. 15, 1992, Duuth, Minnesota US.

"PCR Protocols" Innis et al., 1989 Academic Press, San Diego UP XP002098377 pp. 39-45.

"Improved Double-Stranded DNA Sequencing Using the Linear Polymerase Chain Reaction" Nucleic Acids Research, vol. 17, No. 21 Nov. 1989, p. 8889 XP000371763.

"Automated Cycle Sequencing with Taquenase TM: Protocols for Internal Labeling, Dye Primer and "DoubleX" Simultaneous Sequencing" Biotechnics, vol. 23, No. 2, Aug. 1997, pp. 312-318, XP000698417.

"Cycle Sequencing Using Degenerate Primers Containing Inosines" Biotechnics, vol. 15, No. 1, Jul. 1, 1993, pp. 82, 84, 88-89, XP000385833.

"Point Mutation Analysis in a Mammalian Gene: Rapid Preparation of Total RNA, PCR Amplification of CDNA, and Tag Sequencing by a Novelmethod" Biotechnics, vol. 7, No. 5, May 1, 1989, pp. 494-496, 498/499, XP000406164.

"The Use of a Modified Taq DNA Polymerase for Thermal Cycle Sequencing of Double Strand Plasmid DNA Templates" Spurgeon, S. et al.,Human Genome II. Int'l Conference, Oct. 22, 1990, San Diego, CA.

"Molecular Cloning, a Laboratory Manual" Maniatis, T. et al., published 1982 by McGraw-Hill (NY), see pp. 133, 134 and 143.

"Synthesis of 3-(triethylstannyl) propanioc acid: an organotin mass label for DNA" Sloop et al., Bioconjugate Chemistry. 1993, vol. 4, pp. 406-409.

"Applications of mass spectrometry to DNA sequencing" Jacobsen et al., GATA. 1991, vol. 8, No. 8, pp. 223-229.

"Nucleic Acids: Overview and analytical strategies in: Mass Spectrometry in Biomolecular sceinces." Edited by R.M. Capriolo et al. Netherlands: Kluwer Academic Publishers, 1996, p. 351-379.

"Dual analyte immunoassay for proteins using releasable metal ions as labels (Albumin, immunoglobulin G)." Hayes et al., Dissertation Abstracts International. 1992, vol. 53, No. 9B, p. 4624.

"Covalent modification with concomitant inactivation of the cAMP dependent protein kinase by affinity labels containing only 1-amino acids" Salemo, et al., J. biol. Chem. 1993, vol. 268, No. 18, pp. 13043-13049.

"In Vivo Molecular and Cellular Imaging With Quantum Dots" Gao et al., Current Opinion in Biotechnology, 2005, 16:63-72.

"Luminescent Quantum Dots for Mutilplexed Biological Detection and Imaging" Chan et al. Current Opinion in Biotechnology, 2002, 13: 40-46.

(56) References Cited

OTHER PUBLICATIONS

"Engineered Nanomaterials for Biophotonic Applications: Improving Sensing, Imaging, and Therapeutics" West et al., Annual Review of Biomedical Engineering 2003; 5:285-92.

"Quantum Dots and Other Nanoparticles: What Can They Offer to Drug Discovery" Ozkan Drug Discovery Today, 2004, vol. 9, No. 24, 1065-1071.

"Multiple promoters direct the tissue-specific expression of novel N-terminal variant human vitamin D receptor gene transcripts" Crofts et al., Proc. Natl. Acad. Sci. USA Sep. 1998 95:10529-10534.

Non Final Office Action, Patent No. 6,197,510, Mail Date Nov. 26, 1999.

Cao et al., "A rapid non-selective method to generate quadromas by microelectrofusion," *Journal of Immunological Methods*, 1995, 187:1-7.

Carothers et al., "Point Mutation Analysis in a Mammalian Gene: Rapid Preparation of Total RNA, PCR Amplification of cDNA, and Taq Sequencing by a Novel Method," *BioTechniques*, 1989, 7(5):494-499.

Dakour et al., "Characterization of melanosome-associated proteins by establishment of monoclonal antibodies and immunoscreening of a melanoma cDNA library through an anti-melanosome antibody," *Melanoma Research*, 1993, 3:331-336.

Dakour et al., "Identification of a cDNA Coding for a $Ca^{2+}$-Binding Phosphoprotein (p90), Calnexin, on Melanosomes in Normal and Malignant Human Melanocytes," *Experimental Cell Research*, 1993, 209:288-300.

Hodkinson et al., "Simultaneous Genotyping of Sexually Transmitted Bacterial Pathogens using MULTIGEN Technology," International Society for Sexually Transmitted Diseases, date unknown, 1 page (abstract only).

Jimbow et al., "Molecular Control of Melanogenesis in Malignant Melanoma: Functional Assessment of Tyrosinase and Lamp Gene Families by UV Exposure and Gene Co-Transfection, and Cloning of a cDNA Encoding Calnexin, a Possible Melanogenesis 'Chaperone,'" *The Journal of Dermatology*, 1994, 21:894-906.

Johnson et al., "Genome-Wide Survey of Human Alternative Pre-mRNA Splicing with Exon Junction Microarrays," *Science*, Dec. 19, 2003, 302:2141-2144.

Liu et al., "Molecular Cloning, Sequencing, and Analysis of the cDNA for Rabbit Muscle Glycogen Debranching Enzyme," *Biochemistry and Biophysics*, Oct. 1993, 306(1):232-239.

Le Marechal et al., "Complete and rapid scanning of the cystic fibrosis transmembrane conductance regulator (CFTR) gene by denaturing high-performance liquid chromatography (D-HPLC): major implications for genetic counselling," *Hum. Genet.*, 2001, 108:290-298.

Murray, "Improved double-stranded DNA sequencing using the linear polymerase chain reaction," *Nucleic Acids Research*, 1989, 17(21):8889.

Shen et al., "Cycle Sequencing Using Degenerate Primers Containing Inosines," *BioTechniques*, 1993, 15(1):82-89.

Steffens et al., "Multiplexamplification of STR loci with gender alleles using infrared fluorescence detection," *Forensic Science International*, 1997, 85(1997):225-232.

Sundstrom et al., "Novel Type of Plasmid-Borne Resistance to Trimethoprim," *Antimicrobial Agents and Chemotherapy*, Jan. 1987, 31(1):60-66.

Vinayagamoorthy et al., "Detection of *Giardia lamblia* and *Cryptosoridium parvum* in Water Samples Using Multiplex Sequencing Technology," *American Laboratory*, May 2004, 4 pages.

Vinayagamoorthy et al., "DNA Sequence-Based High-Throughput Microbial Identification Using Multiplex Sequencing," *American Biotechnology Laboratory*, Dec. 2003, 6 pages.

Vinayagamoorthy et al., "Identification of the Severe Acute Respiratory Syndrome Coronavirus by Simultaneous Multigene DNA Sequencing," *Journal of Clinical Microbiology*, Jul. 2004, 42(7):3291-3294.

Vinayagamoorthy, "Identification of West Nile and Other Flaviviruses using Multiplex Sequencing (MultiGEN)," American Society for Microbiology, Polymicrobial Disease Conference, Oct. 19-23, 2003, Lake Tahoe, NV, 1 page.

Vinayagamoorthy et al., "Identifying MRSA with Multiplex Sequencing," *Genetic Engineering & Biotechnology News*, Mar. 15, 2008, 28(6), 3 pages.

Vinayagamoorthy et al., "Molecular Typing of West Nile Virus, Dengue, and St. Louis Encephalitis Using Multiplex Sequencing," *Journal of Molecular Diagnostics*, May 2005, 7(2):152-159.

Vinayagamoorthy, "Rational Drug Design Based on Splice Variants," *Genetic Engineering News*, May 1, 2004, 24(9), 4 pages.

Visible Genetics, Inc., "TruGene™ HIV Genotyping GeneKit™," Jan. 16, 1998, from HIV Genotyping using the OpenGene Automated DNA Sequencing System, Visible Genetics, Inc., Toronto, ON.

Voss et al., "Automated Cycle Sequencing with Taquenase™: Protocols for Internal Labeling, Dye Primer and 'Doublex' Simultaneous Sequencing," *BioTechniques*, Aug. 1997, 23(2):312-318.

Hodkinson et al., "Identification of Food Pathogens Using Multiple Signature Sequences," presented at the 12th World Food Science and Technology Congress, Jul. 16-20, 2003, Chicago, IL, 1 page.

\* cited by examiner

Construction of artificial marker

Construction of artificial marker

| Nucleotide Sequence Based Code to Monitor Cross Contamination | | |
|---|---|---|
| Client code | | ATGTCC |
| Sample: | Swab | ATATA |
| | Urine | GTGTGT |
| Test: | Gonorrhea/ Chlamydia | GCGCGC |
| Position in the 96 well plate | | |
| 1 | SEQ ID NO. 2 | AAACCCTTTGGGAAAA |
| 2 | SEQ ID NO. 3 | AAACCCGGGTTTAAAA |
| 3 | SEQ ID NO. 4 | AAAGGGCCCTTTAAAA |
| 4 | SEQ ID NO. 5 | GGGAAACCCTTTAAAA |
| 5 | SEQ ID NO. 6 | AAATTTCCCGGGAAAA |
| 6 | SEQ ID NO. 7 | TTTAAACCCGGGAAAA |
| 7 | SEQ ID NO. 8 | CCCAAATTTGGGAAAA |
| 8 | SEQ ID NO. 9 | CCCTTTAAAGGGAAAA |
| 9 | SEQ ID NO. 10 | CCCTTTGGGCCCAAAA |
| 10 | SEQ ID NO. 11 | GGGTTTGGGCCCAAAA |
| 11 | SEQ ID NO. 12 | GGGCCCAAATTTAAAA |
| 12 | SEQ ID NO. 13 | GGGTTTAAATTTAAAA |
| Spacer | | TTT |
| | | |

Fig. 4

USE OF MARKERS INCLUDING NUCLEOTIDE SEQUENCE BASED CODES TO MONITOR METHODS OF DETECTION AND IDENTIFICATION OF GENETIC MATERIAL

CROSS-REFERENCE TO RELATED APPLICATION

This application claims the priority right of my prior copending provisional application Ser. No. 60/696,824 filed Jul. 7, 2005.

BACKGROUND OF THE INVENTION

1. Field of the Invention

This invention relates to the analysis or identification of biological samples using nucleic acid detection techniques, such as DNA amplification and sequencing. More particularly, the invention relates to ways of monitoring problems that can arise during such techniques, such as cross-contamination of materials from different sources, as well as enabling sample traceability and providing internal controls for such techniques.

2. Background Art

The technology of molecular biology has opened up number of applications for testing, analysis and diagnosis using nucleic acid techniques (see References 1, 2 and 3 of the References section below). This includes routine testing of clinical, veterinary, end plant samples, as well as development of drugs and specialty bio-pharmaceuticals.

In the early 1990s, a novel nucleic acid amplification technology, polymerase chain reaction (PCR), was made possible. Although the primary use of this technology was targeted at making millions of copies of DNA segments that could be cloned, PCR was later adopted in routine nucleic acid testing, e.g. testing for the presence of infectious microorganisms or specific genes or mutations. Presently, there are number of available assays that use conventional PCR as well as other modifications, such as reverse transcriptase PCR (RT-PCR, used to amplify sequences derived from RNA), ligase chain reaction (LCR), transcription mediated amplification (TMA), etc, to enable the amplification of target nucleic acid molecules having sequences of interest. In addition to target amplification technologies, there are number of signal amplification technologies, such as b-DNA and hybrid capture technology that are presently being used in routine testing. The use of nucleic acids techniques has made routine testing faster so that results can be obtained within hours rather than waiting days or weeks for bacterial cultures to grow.

Whatever the specific technology, routine testing warrants sensitivity (confidence that a negative is true negative) and specificity (confidence that a positive is a true positive). For example, nucleic acids based technologies have to conform to sensitivity and specificity requirements dictated by controlling authorities such as CLIA (Clinical laboratory Improvement Amendment, USA). In addressing these requirements, it has become routine to include, in each batch of testing, one sample without a target that would serve as negative control and one sample with the target as a true positive control, but this increases the complexity and cost of the testing operation. Furthermore, the controls may not be subjected to exactly the same conditions and environment as the actual samples.

Moreover, the fact that extremely small amounts of DNA or RNA may be amplified by PCR and similar technologies means that there is a real possibility of contamination of the samples (i.e. with amplified foreign DNA) employed for testing because small amounts of contaminants may also be amplified and yield an inaccurate result.

Also there is a need for traceability of samples because large numbers of samples are routinely tested and can easily be mixed up. Such sample mix-ups sometimes occur in hospitals and laboratories, so there is also a need for a way of confirming the origin or identity of a particular sample even if there is no contamination as such.

Additionally, ingredients in certain samples (e.g. urine) are known to inhibit target amplification processes, such as PCR or RNA polymerization (References 6 and 7), so there is a need to ensure that there are no inhibitory substances in the samples that could have that effect. In addressing the inhibitory substance issue in the past, artificial targets have been introduced into the samples where the artificial targets will have the same annealing site as that of the target, and the artificial targets produce an amplicon that carries an internal sequence that is different from that of the target (References 4 and 5). Using a third probe specific to this target will detect the artificial target ensuring there are no inhibitory substances. However, this procedure is quite comprised and may not always be reliable.

There is therefore a need for an improved means of monitoring nucleic acid testing techniques.

SUMMARY OF THE INVENTION

One exemplary form of the invention provides a method of testing for the presence of a target nucleic acid in a sample, which method comprises providing amplification primers designed to anneal to the target nucleic acid flanking a characteristic sequence thereof, carrying out a nucleic acid amplification procedure employing the primers to produce an amplicon containing the characteristic sequence, providing a sequencing primer designed to anneal at or adjacent to the characteristic sequence of the amplicon, and sequencing at least part of the characteristic sequence to confirm the presence the target nucleic acid in the sample, wherein a marker is amplified and sequenced as a control at the same time under identical conditions using identical amplification and sequencing primers, the marker having a unique nucleotide sequence flanked by annealing sites for the amplification and sequencing primers.

The unique sequence preferably comprises a coding region of nucleic acid bases that encodes specific information according to a predetermined code.

Another exemplary embodiment provides a method of carrying out a test for a target nucleic acid sequence in a sample, which method comprises carrying out a nucleic acid amplification procedure designed to produce amplicons containing a characteristic part of the target sequence, if present in the sample, and carrying out a sequencing procedure designed to reveal the presence of amplicons containing the characteristic part, thereby confirming the presence of the target nucleic acid in the sequence, wherein the results of the sequencing procedure are also investigated for indication of the presence of amplicons containing a predetermined coded sequence from one or more artificial markers, and, if found, decoding the coded sequence(s) to obtain information contained in the marker(s).

The artificial marker may be added to the sample prior to carrying out the nucleic acid amplification and sequencing steps, thus forming an internal marker, and may include, in addition to the coded sequence, nucleic acid sequences that allow amplification and sequencing of the coded sequence simultaneously with amplification and sequencing of the characteristic part of the target nucleic acid sequence.

Another exemplary embodiment of the invention provides a method of testing for the presence of a target nucleic acid sequence in a sample, which method comprises providing amplification primers designed to anneal to the target nucleic acid flanking a characteristic part thereof, carrying out a nucleic acid amplification procedure employing the primers to produce an amplicon containing the characteristic part of the target nucleic acid sequence if the sequence is present in the sample, and sequencing at least part of the amplicon if thereby produced to reveal the characteristic part of the target nucleic add sequence, wherein a marker is introduced into the sample prior to the amplification procedure, the marker having a unique nucleotide coding sequence encoding specific information flanked by nucleotide sequences that permit the coding sequence also to be amplified and sequenced as the characteristic part of the target is amplified and sequenced, thereby revealing the specific information corresponding to the coding sequence as well as the presence or absence of the target nucleic acid sequence in the sample.

Preferably, the nucleic acid amplification procedure involves polymerese chain reaction and the nucleotide sequences that permit the coding sequence to be amplified include sequences that anneal to primers used for the amplification of the target sequence.

Another exemplary form of the invention provides a method of enabling positive identification of an item, which comprises adding to the item a marker including a coded nucleic acid sequence containing information about the item, and sequences that permit amplification and sequencing of the coded nucleic add sequence.

Another exemplary form of the invention provides a marker comprising a molecule including a nucleic acid sequence, the sequence comprising an artificial coding sequence that may be decoded to reveal specific information, and regions that permit amplification and sequencing of the coding sequence.

Preferably, the invention uses coded artificially-generated nucleotide sequences in the same assay as a target sample to (a) detect cross-contamination if it occurs, (b) trace the origin of samples, and/or (c) ensure that there we no inhibitory substances in the assay.

The invention may also be applied to the detection of trace contamination in other processes as well as processing equipment such as Tripath® thin preparation, and may also be employed during the manufacture of biopharmaceuticals, validating filtration (filter validation), and the like.

The term "amplicon" as used herein means a molecule or collection of molecules (population) obtained by amplifying a particular nucleic acid sequence by a nucleic acid amplification technique, e.g. PCR or RT-PCR.

The invention may be used in the following ways (among others).

Cross-Contamination

During DNA-based amplification technologies, in particular, cross-contamination of a sample may occur at any stage of the procedure, for example, as follows:

A target from another sample may be accidentally introduced as a cross-contaminant.

An inhibitory substance from another sample may be introduced as a cross-contaminant.

There may be a general contamination at the site of sample collection (e.g., in the laboratory or at physician's office, etc).

The reagents that are used in the assay may be contaminated with target(s).

The consumables used in the assay could be contaminated with the target(s).

Samples may be contaminated on receiving and initial processing at a laboratory.

Samples may be contaminated during processing particularly using 96-well plates.

Presently there are no sensitive methods that can detect these cross-contaminations. The present invention provides a technique that can detect cross-contamination. It does not prevent cross-contamination, but it enables it to be detected if it does occur.

If there is cross-contamination of samples, the artificial codes of two or more markers will be revealed instead of just one, and the information in the markers can be used to reveal where the cross-contamination came from.

Traceability

If a sample containing a marker is of unknown origin, the sample may be amplified and sequenced and, if the artificial code of the marker is thereby revealed, the information in it will reveal the source and details of the sample (depending on the information encoded into the coding sequence).

The processing of large numbers of samples is a challenge, especially during routine testing. Sample mix-up is one of the common errors in routine testing. Although external identification systems, such as bar code identification, etc., are commonly employed, they are still subject to human and/or mechanical error. The present invention provides a built-in nucleotide sequence based coding sequence that may identify, for example, the customer, type of sample (urine or swab), test requested (e.g. *Chlamydia trachchomatis* and *Neisseria gonohrrea*), well-position in the testing equipment or 8 well strip or 96 or 384 well plate, etc.

Inhibitory Substances

If a marker according to the invention is added to a sample that may contain inhibitory substances and the usual amplification and sequencing is performed, the presence of amplicons containing the coding sequence will show that the amplification and sequencing procedures were not inhibited by any substance present. The absence of amplicons containing the sample sequence will then show conclusively that the expected target DNA or RNA was not present in the sample. Alternatively, the absence of the artificial sequence, will show that the amplification and sequencing was inhibited.

The invention has the advantage that the marker molecule and the sample molecule are subjected to exactly the same environment and procedures, so the results are highly reliable.

Construct of the Control Target

The marker molecule may be constructed and encoded to have, for example, the following potential uses:

Traceability:
customer identification sequence
sample type identification sequence
test identification sequence
Cross-Contamination/Traceability:
well identification sequence
Internal Positive Control
PCR primer annealing sequences
Sequencing primer annealing sequences Ideally, the coding sequence of the marker will have the sequence codes flanked by both the upstream and the downstream target amplification primers, as well as including an annealing site for the sequencing primer that is designed for the sample target molecule. Use of such a marker will not only insure that the PCR primers are annealing to the sample target in the sample conditions, but also that the PCR process is not inhibited. Similarly, the sequencing primer anneals both to amplicons produced from the sample target as well as amplicons produced from the marker, and confirms that the polymerization required for sequencing is not inhibited in both the target and the marker.

Markers having different codes may be used either separately as independent batch controls in separate wells, or, more preferably, mixed with the clinical samples as internal controls for each sample. When the marker is used in combination with clinical samples as an internal control, the construct will preferably have a homogenous nucleotide sequence (e.g. polyA, polyG, polyT or polyC) preceding the first coding cluster (e.g. the customer identification sequence). The length of the homogenous nucleotide sequence will preferably be longer than the target sequence that will be produced by the sequencing primer annealing to the test target from the clinical sample.

Coding Sequence

In one form of the invention, the marker merely includes a unique sequence of bases that distinguishes the marker amplicon from that of the sample target. This is the simplest form of code merely identifying the sequence as belonging to the marker and not to the target nucleic acid. More preferably, however, the marker includes (as said unique sequence or part thereof) a more complex coding region in which nucleotide bases are used as coding symbols to represent any of a number of parameters associated with routine testing. This could involve nucleotides present in DNA, RNA or a combination or modification of these nucleotides.

The coding region may contain, for example, nucleotide sequences incorporating specific codes for one or numerous factors. Typical factors include codes for:
 i. Customer (e.g. Name of a hospital)
 ii. Sample type (Swab or urine)
 iii. Test ordered (*Chlamydia*, trachoma is, *Neisseria gonorrhea*)
 iv. Position in a 96 well plate.

Analysis

The combination of a coded marker and target sequence subjected to amplification and sequencing will generate two groups of truncated polynucleotide chains, i.e.

a. One generated from the sequencing primer annealing to the test target in the clinical sample. This will normally generate a short (25-35 base) target-specific nucleotide and the nucleotide sequence of the downstream PCR primer.

B. One generated from the sequencing primer annealing to the marker target will produce a nucleotide sequence preferably starting with a polynucleotide followed by the other elements of the control construct, including the coding region and the nucleotide sequence of the downstream PCR primer.

In the absence of expected target from the clinical sample, only the nucleotide sequence generated by the sequencing primer annealing to the control target will be observed.

If an expected test target is present in the clinical sample, then both A and B will be present and sequences from both will be generated. The observed electropherogram will have a signal overlap in the initial section of sequence read followed by a clear signal. The overlap section will have the test target specific sequence and the downstream PCR primer generated by the sequencing primer annealing to the true positive target in the sample that overlaps with the polynucleotide sequences generated by the same sequencing primer annealing to the control target. In order to analyze the electropherogram, the channel corresponding to the homonucleotide sequence (e.g. polyA, etc.) will be turned off on the sequencing mafcins and the target sequence will be analyzed (homology matching) using the sequence based on the remaining three nucleotides.

The distal part of the electropherogram will then be mainly from the truncated molecules generated by the sequencing primer annealing to the marker. Since the distal part of the electropherogram will not have any overlap all four channels may be turned on for analysis of the nucleotide sequences produced from the marker.

It should be noted that the present invention may be used in combination with the technology disclosed in U.S. Pat. No. 6,197,510 issued on Mar. 6, 2001 to Thuraiayah Vinayagamoorthy (the disclosure of which is incorporated herein by reference) and referred to by the trademark MultiGEN® (see also Ref 8). This is a platform technology that allows for simultaneous determination of nucleotide sequences from multiple genomes or multiple segments from the same genome or a combination of both. This technology mainly involves three steps:

(a) Preparation of total nucleic acid from the sample (this could be nucleic acids, RNA, or both);
 (b) Simultaneous amplification of all target genomes (this can be carried out by any suitable target amplification method including PCR), and
 (c) Simultaneous sequencing at the 3'-end of all amplicons.

The sequences generated may be identified by a BLAST search. The test protocol will vary based on the type of genomic targets to be analyzed (nucleic acid, RNA, or both), the number of targets (2-20 are feasible), and the expected copy number of the targets in the samples. The present invention may be used in this technology by introducing the marker into the sample and amplifying and sequencing the resulting amplicon along with the others produced from the numerous genomes.

Apart from use in routine testing, this invention also can be used in securing and traceability of valuable items such as, painting, jewels, and paper and other documents. This can be achieved simply by incorporating a marker according to the invention into the item, the marker encoding information about the item. Amplification and sequencing will then reveal the encoded information when required.

BRIEF DESCRIPTION OF THE DRAWINGS

FIG. 4 is a table showing an example of nucleotide sequence based coding system that may be used to incorporate information into a marker molecule;

DETAILED DESCRIPTION OF THE PREFERRED EMBODIMENTS

Figure 1:
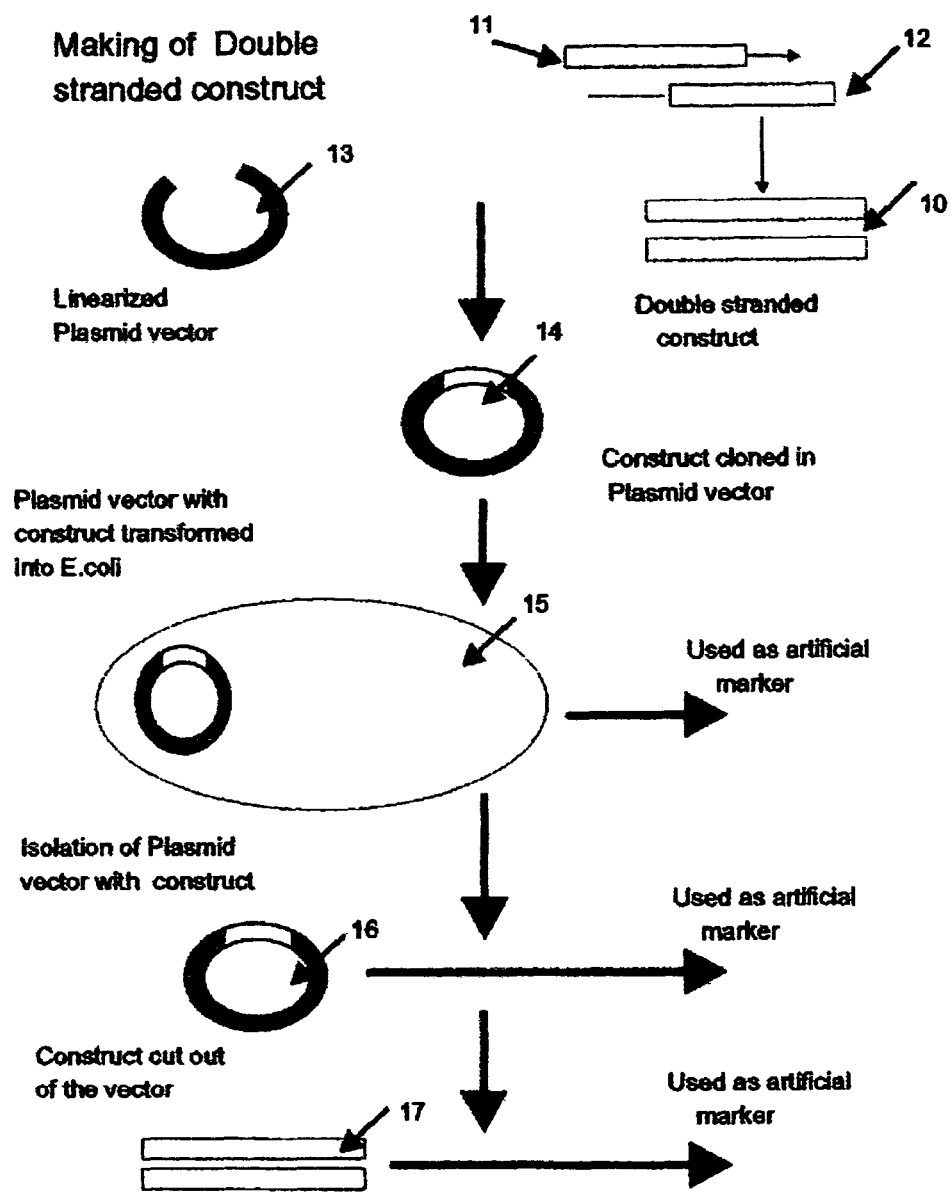
FIG. 1 is a diagram illustrating one preferred way of constructing a marker according to one form of the present invention.

The present invention, at least in one preferred form, makes use of the genetic code (the sequence of As, Cs, Ts, Gs, Us representing the bases present in nucleic acids, i.e. adenine, cytosine, tyrosine, guanine and uracil, respectively) to create predetermined unique artificial codes (i.e. unique short sequences that are not likely to be encountered in sample targets that will undergo testing) that can be used as identifiers (sometimes referred to as "signatures") of materials of a particular kind, origin or treatment. The invention also preferably provides a means by which the code can be multiplied and revealed.

Short stretches of artificial DNA or RNA (e.g. up to 100 nucleotides) are routinely synthesized by nucleic acid polymerization methods, e.g. for the preparation of primers used for PCR procedures, so such short stretches can be made to have any desired sequence of the "letters" of the genetic code (i.e. a coding sequence forming a coding region of the artificial molecule), and particular combinations of those letters can be designated to have particular meanings. The artificial sequence (coding region) may then be flanked by amplification primer annealing sequences (e.g. for upstream and downstream PCR primers), i.e. by short stretches of nucleic acids having sequences that will anneal with primers designed for subsequent nucleic acid sample amplification and sequencing procedures intended for sample identification. The resulting artificial sequences (preferably also provided with restriction enzyme recognition sites, e.g. Ecor1, HindIII or BamHI, etc., flanking the other sequences) may then be incorporated into DNA or RNA constructs (vectors) using cloning techniques to create double stranded markers that may be added to samples or sample wells, or used as controls. When such a marker is present in a sample and the sample is subjected to amplification and sequencing of a characteristic portion of a sample DNA or RNA, the marker sequence is also amplified and sequenced at the same time. The sequencing procedure reveals the coded region which may then be decoded (by reference to the original code either manually or by computer), and the information thereby obtained may be used for testing, identification or control purposes. The sequencing procedure normally makes use of a sequencing primer and the invention provides a corresponding annealing site for the proposed sequencing primer upstream of the coding sequence.

By making the PCR primer annealing sites and the sequencing primer annealing sites of the marker correspond to (i.e. anneal to) the polymers intended for target sample testing, the present invention, at least in one preferred form, allows both the genomic sequence of the target and the coding region of the marker to be amplified and sequenced at the same time, under the same conditions, and in the same solution and equipment. The coded information can then be used to derive information about the sample sequence or other conclusions of interest.

The techniques involved in PCR, RT-PCR and nucleic acid sequencing are well known and are disclosed, for example, from: Molecular Cloning: A Laboratory Manual, by Sambrook and Russel, 3rd Edition, Cold Spring Harbor Laboratory Press, 2001 (the disclosure of which is incorporated herein by reference).

Details of cycle sequencing are also disclosed, for example, in Hisashi Yamakawa and Osamu Ohara, "A DNA Cycle Sequencing Reaction that Minimizes Compressions on Automated Fluorescent Sequencers", *Nucleic Acid Research*, Vol. 25, No. 6, pp. 1131-1312, the disclosure of which is also incorporated herein by reference).

Briefly stated, in chain terminator sequencing (Sanger sequencing), nucleic acid extension is initiated at a specific site on the substrate DNA acting as a template by using a short oligonucleotide sequencing primer" complementary to the template at that site. The oligonucleotide primer is extended using a DNA polymerase in the presence of the four deoxynucleotide bases (DNA building blocks), along with a low concentration of a chain terminating nucleotide (most commonly a dideoxynucleotide). The primer or, more commonly in dye termination sequencing, the dideoxynucleotides, are provided with a fluorescent tag (e.g. a fluorescent tag having a different wavelength representing each base). As the DNA strand is elongated, the DNA polymerase catalyses the joining of deoxynucleotides to the corresponding bases. However, if a dideoxynucleotide is joined to a base, then that fragment of DNA can no longer be elongated since a dideoxynucleotide lacks a crucial 3'-OH group. Fragments of all sizes are obtained due to the randomness of the addition of the dideoxynucleotides. The DNA is then denatured and the resulting fragments are separated (with a resolution of just one nucleotide) by gel electrophoresis, from longest to shortest, in a slab polyacrylamide gel or more commonly, in a narrow glass tube (capillary) filled with a viscous polymer (e.g. POP 7® polymer, Applied Biosystems, USA). The fluorescent signals may then be read simultaneously with a four-channel wavelength detection device (e.g. an ABI PRISM® 3100 Genetic Analyzer capillary gel electropherometer), and the resulting peaks represent individual nucleotides of one of the four kinds.

Further details of preferred ways in which preferred forms of the present invention may be carried out and employed are provided below with reference is made to the accompanying drawings.

FIG. 1 is a diagram providing an overview of a preferred procedure for making a marker according to the Invention. First of all, a double-stranded construct 10 is produced. The easiest way to do this is to prepare two single stranded artificial construct parts 11 and 12 each with sequence regions that anneal together so that each part may be extended with sequences complementary to the other using chain extension techniques (the nature of u the construct will be explained in more detail later). The double stranded construct 10 is then ligated into a linearized plasmid vector 13 and re-circularized (e.g., using the methods of TOPO® TA cloning, Invitrogen, USA). The resulting vector 14 is introduced into a cell of, for example, *E. coli* strain JM 101 or One Shot® Chemically Competent TOP 10 *E. coli*, using standard cloning techniques and grown with corresponding antibiotic selection.

The resulting double stranded marker may be used in the form of cells 15 of the organism containing the plasmid incorporating the construct, in the form of the isolated and purified plasmids 18 themselves, or in the form of the digested part 17 of the plasmid containing the construct with the coding elements.

Figure 2:
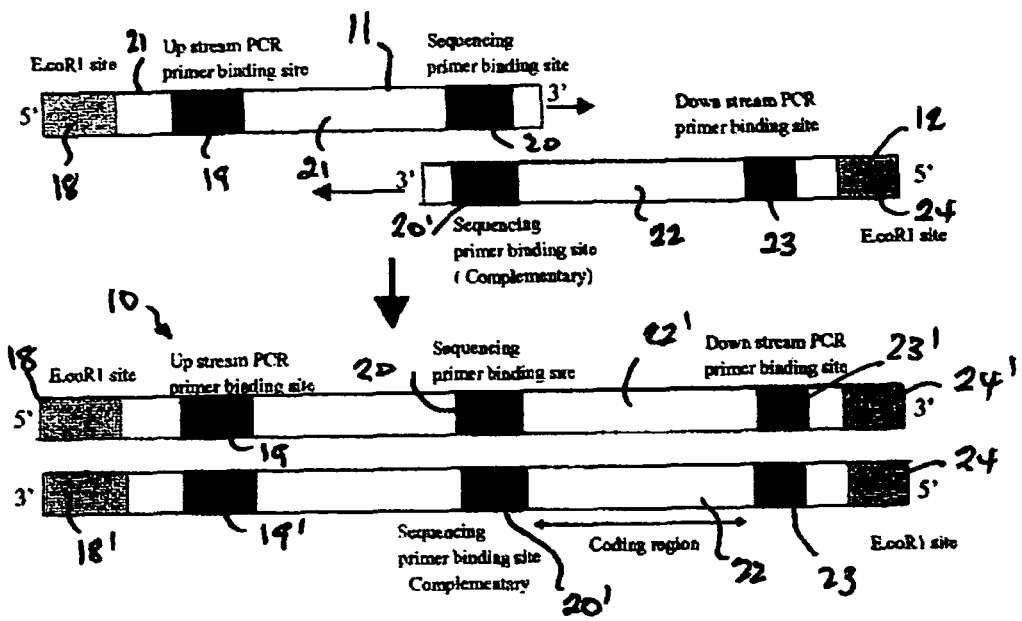
FIG. 2 is a diagram illustrating a preferred way of carrying out one of the steps of FIG. 1.

FIG. 2 shows in more detail one of several preferred ways of making the artificial construct. Using known DNA synthesizing techniques, two construct parts may be formed, each, for example, of approximately 70 mer in length (using the methods of Integrated DNA Technologies, USA, for example). One part 11 (as shown at the upper left hand side of FIG. 2) may consist (in order from the 5'-end), of an EcoR1 recognition site 18, an upstream PCR primer binding site 19, and a sequencing primer binding site 20, which sites may be separated by unspecified DNA 21. The second construct part 12 may consist (from the 3'-end) of the complement 20' to the sequencing binder site, a coding region 22, a downstream PCR primer binding site 23 and an EcoR1 site 24. As shown in FIG. 2, a double stranded construct 10 contains the EcoR1 recognition site 18, the upstream PCR primer binding site 19, the sequencing primer binding site 20, a complement 22' to the coding region 22, a complement 23' to the downstream PCR primer binding site 23 and a complement 24' to the EcoR1 site 24. The complementary strand contains a complement 18' to the EcoR1 recognition site, 18, a complement 19' to the upstream PCR primer binding site, a complement 20' to the sequencing primer binding site, the coding region 22, the downstream PCR primer binding site 23 and an EcoR1 site 24.

When mixed together under annealing conditions, the construct parts will anneal at the sequencing binder site 20, 20', and the annealed construct can be chain-extended in the direction of the arrows as shown using known methods to produce a double-stranded DNA molecule 10 with each part having the full length and complementary sequences.

Of course, it is not essential to use the amplification primer sites or the sequencing primer site as the annealing regions for the two construct parts 11 and 12 because any mutually complementary region of the primers could be designed for this purpose.

When the resulting marker containing these sequences is amplified by PCR, an amplicon will be generated that will have PCR primer sequences at both ends with a sequencing primer in between and the coding sequence between the sequencing primer and one of the PCR primers.

Figure 3:
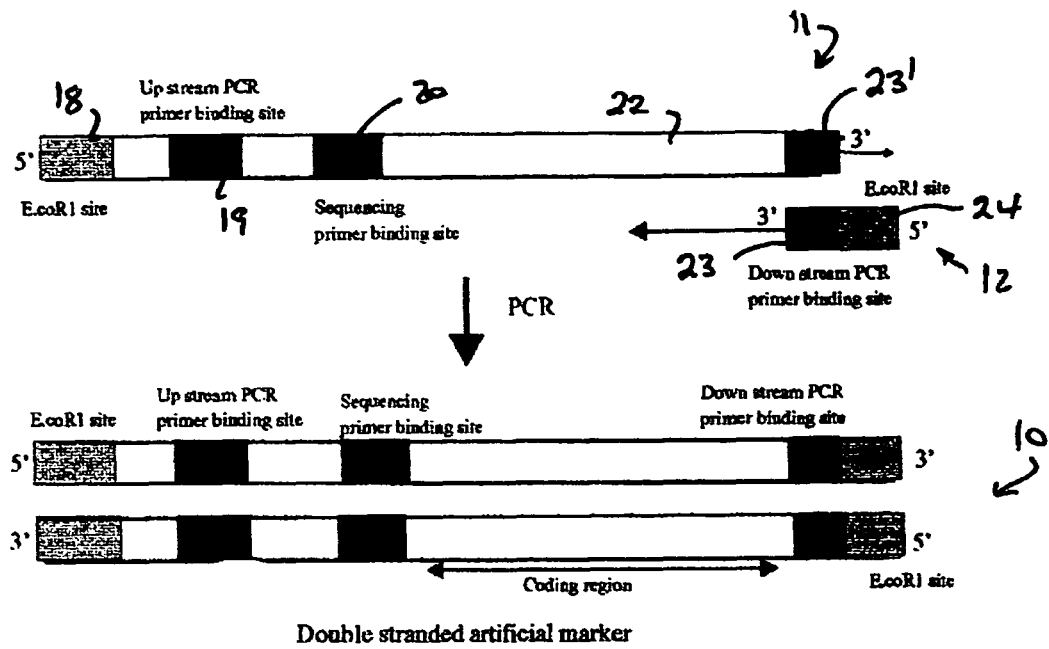
FIG. 3 is a diagram illustrating an alternative to the step of FIG. 2.

FIG. 3 shows a modification of the procedure of FIG. 2, where the first construct part 11 contains virtually the whole of the construct sequence and the second part 12 just comprises the downstream PCR binder site 23 and the EcoR1 site 24, but again the double stranded construct is produced by chain extension in the direction of the arrow as shown.

As already noted, in the coding region 22, nucleotides are used as coding symbols to represent any of a number of parameter associated with routine testing.

The variables may be coded using either
 i. one nucleotide e.g. A
 ii. two nucleotides e.g. AA
 iii. three nucleotides e.g. AAA
 iv. or any number of nucleotides, e.g. AAAAAAAA
 v. any combination of nucleotides, e.g. ATG or ATTGT.

Of course, the higher the number of nucleotides used for a specific factor, the greater the amount of information that may be included (the use of a single nucleotide, for example, would enable the coding of only four pieces of information represented by the bases A, C, T (U) or G.

The letters may be spaced along the coding sequence in clusters representing different factors or kinds of information, if necessary separated by recognizable spacers (e.g. a cluster of three or more identical letters). The position of a cluster along the coding sequence may be used to identify the factor that a particular cluster represents (e.g., in the 5' to 3' direction, first comes the customer identification cluster, then the tope of sample duster, etc.

An example of a code that may be incorporated into a coding region is shown in the table of FIG. 4. The full coding sequence will be a combination of the sequence parts (clusters) shown in the table. For example, a first part of the artificial sequence (i.e. first cluster of nucleotides) may identify a particular client (person or organization that supplies samples) and this may be, for example, the sequence ATGTCC as shown (a different unique sequence would be used for a different client). There may then be sequences intended to identify a particular type of sample, i.e. a swab (ATATA) or urine (GTGTGT), what the test is intended to find (Gonorrhea/Chlamydia-GCGCGC), the row of the plate (one of the 12 sequences shown for a common 96-well plate), and there may be a spacer sequence (e.g. TTT) intended to show the start and end of one or more of the other sequence 25 clusters). A specific sequence for a particular marker might then be as follows:

(SEQ ID. NO: 1)
ATGTCCTTTATATATTTGCGCGCTTTAAACCCTTTGGGAAAA which would indicate a particular client with a sample from a swab being tested for gonorrhea and inserted into a well in row 1 of a 98-well plate.

The coding sequence above may also be provided with a lead-in sequence designed merely to make the resulting amplicon larger (of greater length) so that results obtained during sequencing will not overlap with those from the amplicon derived from the sample sequence (see later). For example, the coding sequence may be provided with an homogeneous sequence, such as a 27 mer poly-A lead-in sequence.

As shown in FIGS. 2 and 3, the coding sequence will then be flanked by sequences that will anneal to upstream and downstream PCR primers intended for use with the sample tests (e.g. intended to amplify and sequence a section of the genome of the organism that produces gonorrhea) and also a sequence that will anneal to a sequencing primer also intended for the sample tests.

Figure 5:
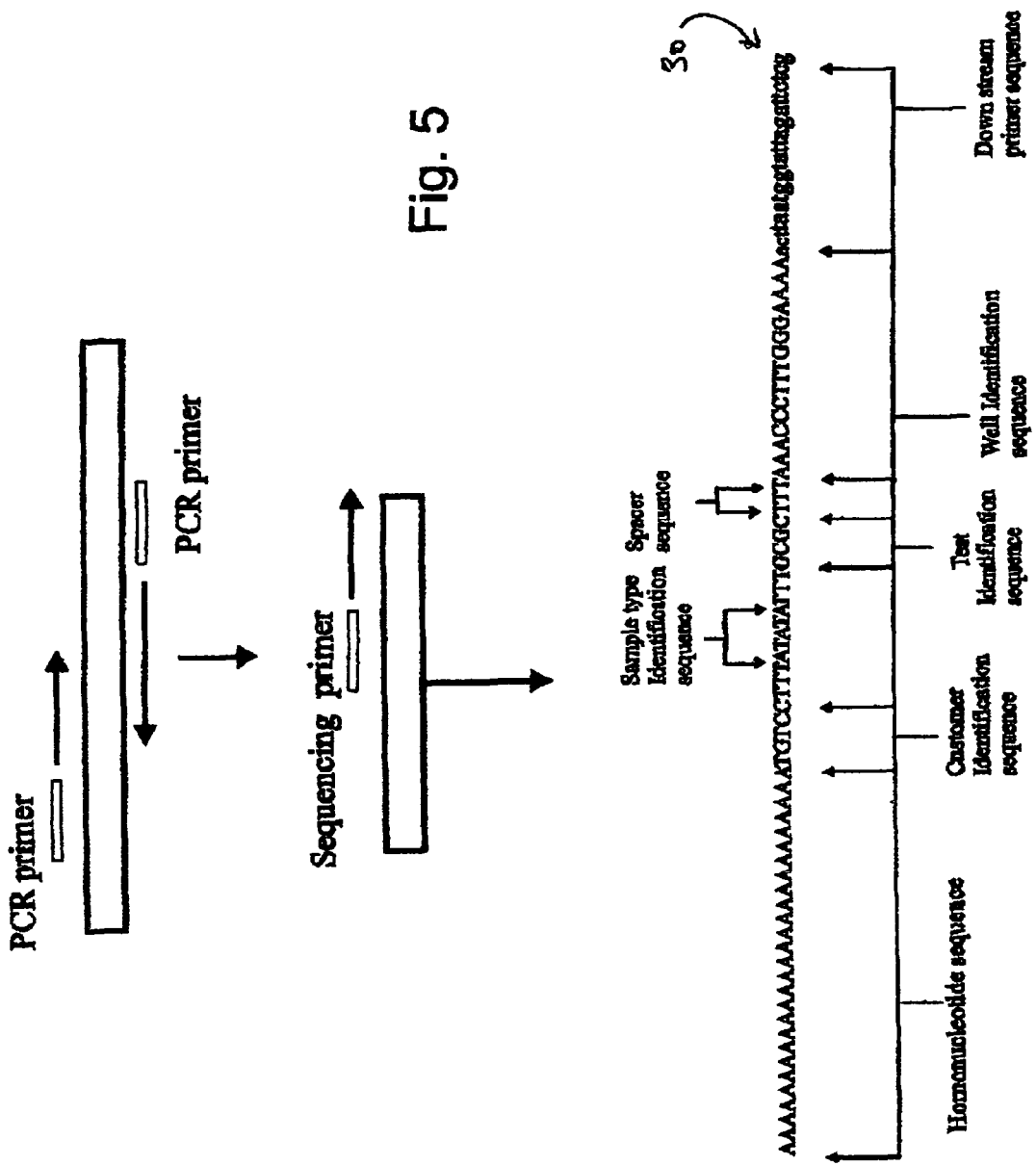
FIG. 5 is a diagram illustrating the amplification and sequencing of a marker according to one preferred form of the present invention.

In use, such a construct, when amplified and sequenced, will reveal a sequence 30 as shown in FIG. 5. The information in the sequence can then be decoded (either manually or automatically using a computer) from a table such as the one shown in FIG. 4.

Figure 6:
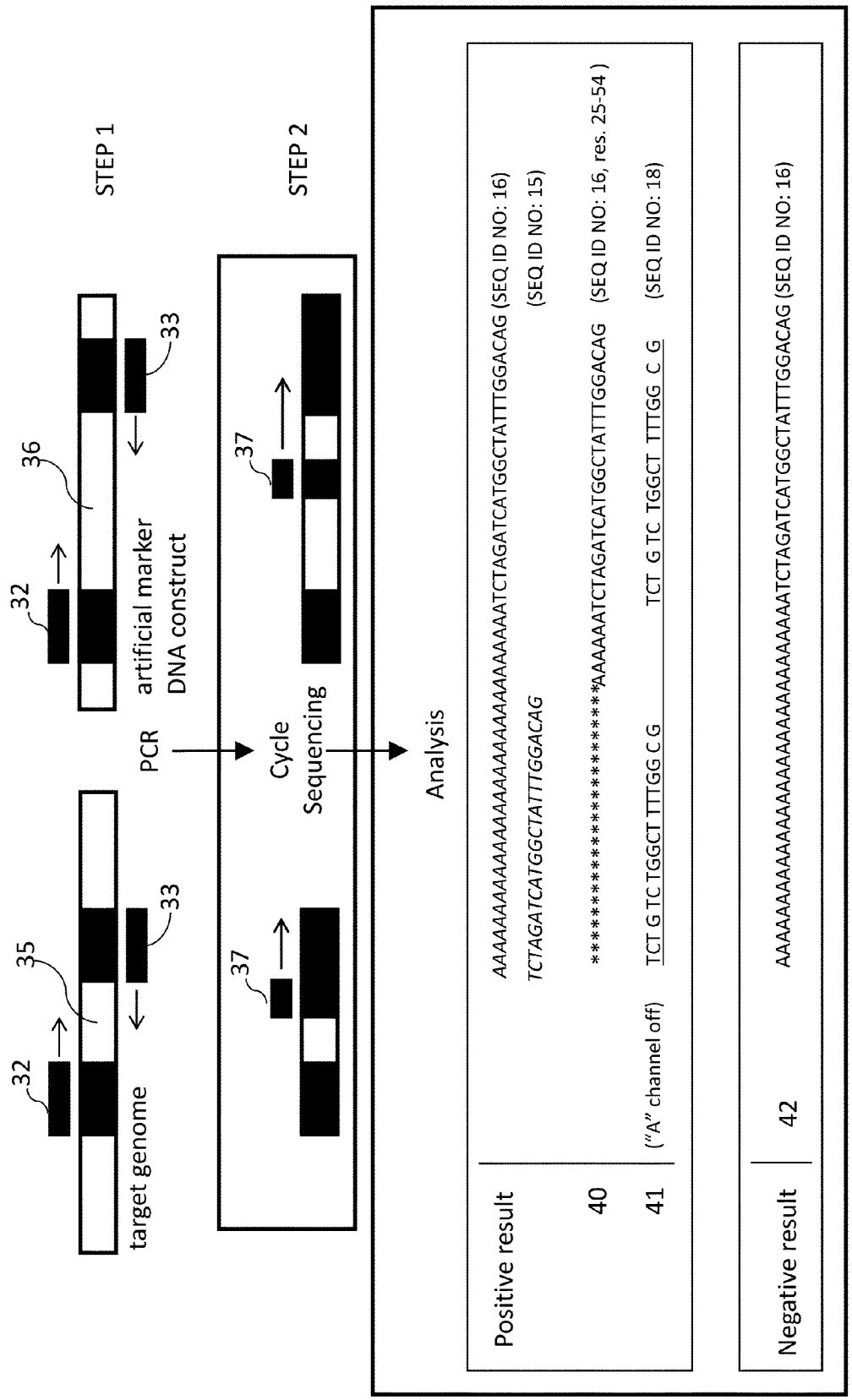
FIG. 6 is a diagram illustrating simultaneous amplification and sequencing of a marker and a target genome sequence according to one is preferred form of the invention, item 40 show the overlap between the expected target sequence (SEQ ID NO. 15) and the expected sequence from the artificial construct (SEQ ID NO. 16)

The events that will take place when both a marker and a target are present in the sample are represented in FIG. 6. It should be noted that, in this figure, the coding region of the marker is different from that shown in FIG. 5 and disclosed above. In STEP 1 as shown, PCR primers 32 and 33 added to the sample to produce amplification of the sample target sequence 35 also produce amplification of the artificial marker 36 As shown in STEP 2, sequencing primer 37 added for cycle sequencing of the sample target amplicon (left-hand side) will also result in sequencing of the artificial marker amplicon (right-hand side). The expected target sequence (SEQ ID NO: 15) and the expected sequence from the artificial marker construct (SEQ ID NO: 16) following cycle sequencing are shown. In analysis, the measured result 40 will show an overlap of nucleotides from both amplicons (indicated with *s in 40 and with text set forth in italics in the expected target and marker sequences), but if the marker amplicon contains a poly-A sequence of suitable length at the start (at least as long as the expected sample target sequence), the A channel of the nucleotide detector may be turned off to reveal the sample target sequence (with missing As) followed by the coded marker sequence (with missing As) as shown at 41. If the sample target sequence is missing, thereby proving a negative result for the presence of the genomic target, only the marker sequence 42 will be revealed (it may not be necessary to switch off the A channel if it is clear that there is no nucleotide overlap in the result).

Figure 7:
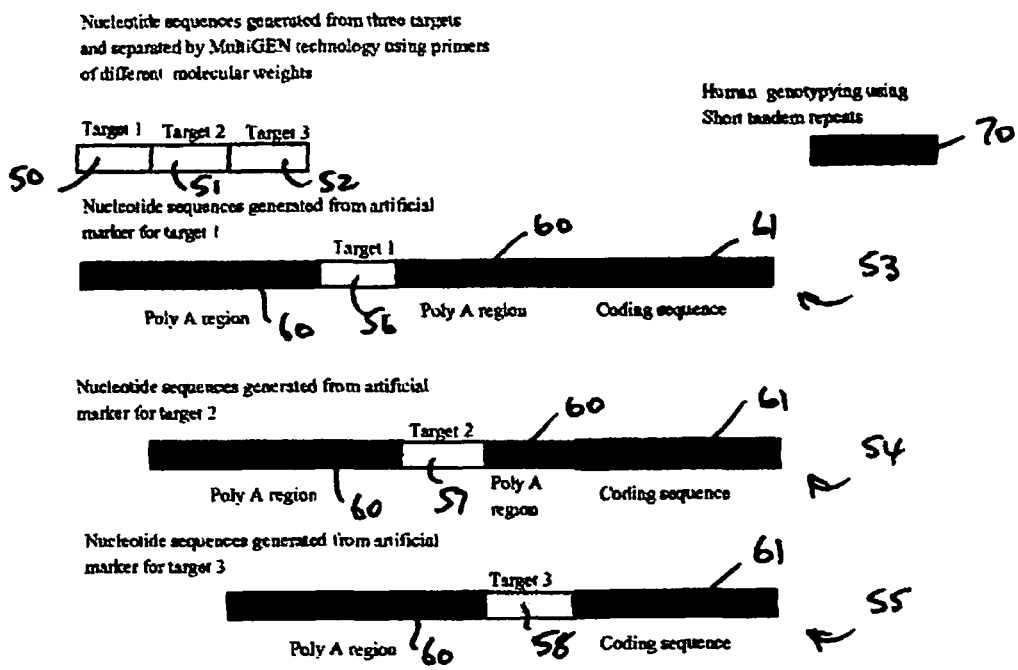
FIG. 7 is a diagram showing three marker constructs and target genomes intended for use when three target genomes are tested simultaneously and genotyping using STRs is also carried out.

FIG. 7 illustrates a more complex application of the present invention intended to be used with the so-called MULTIGEN® technology disclosed in U.S. Pat. No. 6,197,510. Briefly, the MULTIGEN® technology is a way of amplifying and detecting two or more genomic targets at the same time by making the amplification primers designed for the different targets to be of different molecular weights so that the resulting amplicons are of different sizes, thereby allowing separation by gel electrophoresis (Ref. 8). The figure shows three different genomic targets 50, 51 and 52 represented as Target 1, Target 2 and Target 3, and three marker sequences 53, 54 and 55 (the regions of the markers that will be revealed by cycle sequences), one of which includes a sequence 56 corresponding to Target 1, another 57 corresponding to Target 2 and a third 58 corresponding to Target 3. The markers themselves will contain annealing sites for the PCR primers used for the corresponding genomic targets, and sites for the corresponding sequencing primers. The concept is that, if amplification and sequencing reveals an amplicon containing Target 1, for example, then the conditions for amplification and sequencing of genomic Target 1 are operational, and the absence of a corresponding genomic sequence containing Target 1 will confirm that the genomic target is not present.

Each of the three marker constructs contains (in the 5' to 3' direction) at least one poly-A region 60 on one or both sides of the target sequence, and a final coding sequence 61. However, the poly-A regions of the three constructs are of such a size and position that, in the output of the electropherogram:

a. only poly-A regions overlap the sequences from the genomic targets (which themselves do not overlap, as represented at the top of FIG. 7, because of the use of sequencing primers of different lengths);

b. the sequences 56, 57 and 58 for Target 1, Target 2 and Target 3 derived from the three markers do not overlap;

c. the coding sequence 61 from each marker is identically aligned in the output and hence produce a clearly readable result (because the coding region for each marker will be the same).

Consequently, by turning off the A channel of the electropherogram, all of the sequences of interest (if present in the sample) will be unambiguously aligned in the electropherogram (minus As), thus: Target 1 (genome), Target 2 (genome), Target 3 (genome), Target 1 (marker 1), Target 2 (marker 2), Target 3 (marker 3), coding sequence (marker—providing information).

The poly-A regions on each side of the target region of the three markers are adjusted to produce these results (with the marker 55 having no poly-A region on the downstream side of the Target 3 region 58). It will be seen that the sequenced parts of the three markers are not aligned at the left hand side of the figure, and that the third marker is indented to the right more than the second marker, and the second marker is indented to the right more than the first marker. This represents the different positions at which the read-outs of these parts will commence in the electropherogram due to the use of sequencing primers of different (progressively larger) molecular weight for the three targets 1, 2 and 3 designed to prevent overlap of the read-outs of the target sequences themselves.

Testing of this kind may be carried out while simultaneously carrying out human (or other) genotyping by detecting short tandem repeats (STRs). This can be done by designing amplification primers for the STR regions of the sample and then separating the resulting amplicons from the others by gel electrophoresis. By using primers of greater length than those used for the genomic targets and the markers, the resulting amplicons for STR will be spaced from the other amplicons during electrophoresis (as represented by their position 70 to the right hand side of FIG. 7). The primers used for the STR amplification are labeled (one primer of each pair) with a fluorescent (or other) tag, whereas the other amplification primers are not, and U is used in place of T in the construction of the STR primers alone. Therefore the STR amplicons will be detectable by the electropherogram (by virtue of their fluorescent tag) even though these amplicons are not sequenced, and the results will show up spaced from the results for the genomic targets and the markers. Sequencing of these amplicons is avoided by not including sequencing primer sites into the STR amplicons and removing PCR and STR primers after the amplification step, but before the cycle sequencing step. There are two main ways in which the PCR and STR primers may be removed, i.e.:

a. Physical methods Physical methods e.g. membrane filtration (for example, using the equipment of Millipore, USA);

b. Chemical methods e.g. the use of Amplirase (Urasil-N-Glycolysase, Applied Biosystems USA). When a PCR reaction mixture is digested with Amplirase, the enzyme digests into bits and pieces (at the base 'U') all primers that are not incorporated as well as the primers that are incorporated into the amplicons. The labeled primer for the STR is made in such a way that the first nucleotide other than U from the 3'-end is labeled with a fluorescence marker. There is no U between the labeled nucleotide and the 3'-end of the STR primer. Hence the labeled nucleotide incorporated into the STR amplicon is not removed.

After the clean up, the reaction mixture will contain unlabeled target amplicons and artificial marker amplicons and labeled STR amplicons only. When proceeding with regular cycle sequencing, the STR amplicons formed will not have any binding sites for those primers used in the cycle sequencing step, but will carry the fluorescence labels. Therefore the STR amplicons will light up and the molecular weights of STR primers are such that the amplicons signals will show outside all the signals produced from cycle sequencing and will not be involved in any sequence analysis.

Figure 8:
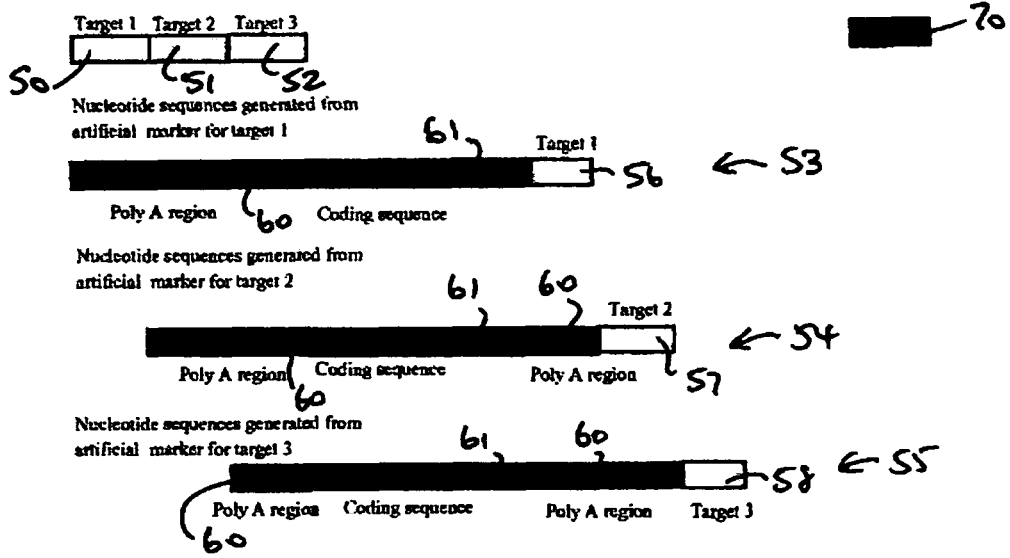
FIG. 8 is a diagram similar to FIG. 7 showing alternative marker constructs.

FIG. 8 is a diagram similar to FIG. 7, but showing the three constructs designed in a different way to achieve the same result. In this case, the coding regions (identical in all three cases) are positioned centrally of the constructs and precisely aligned with each other, with the Target 1, 2 and 3 sequences staggered at the 3'-ends to avoid overlap. The poly-A regions of the three constructs are adjusted in length to achieve this result and to compensate for the differences in length of the sequencing primers used for the genomic targets. Again, STR may be carried out simultaneously in the same way as before, and the resulting electropherogram (when the A channel is turned off) avoids overlap of the sequences of interest, even if all such sequences are present.

In some embodiments, the methods of this invention include a method of testing for the presence of a target nucleic acid in a sample, which method comprises providing amplification primers designed to anneal to said target nucleic acid flanking a characteristic sequence thereof, carrying out a nucleic acid amplification procedure employing said primers to produce an amplicon containing said characteristic sequence, providing a sequencing primer designed to anneal to said amplicon at a position effective for sequencing said characteristic sequence of said amplicon, and sequencing at least part of said characteristic sequence to confirm the presence said target nucleic acid in said sample, wherein a marker is amplified and sequenced as a control at the same time under identical conditions using identical amplification and sequencing primers, the marker having a unique nucleotide sequence flanked by annealing sites for said amplification and sequencing primers, wherein said target nucleic acid includes a plurality of different characteristic sequences, and amplification and sequencing primers are provided for each one of said plurality of different characteristic sequences, and wherein an equal number of markers as said plurality of different characteristic sequences is provided, each of said markers having a different unique sequence including at least a part identical to one of said characteristic sequences, the part that is identical to one of said characteristic sequences being different in each marker.

The following Example is provided to further illustrate the present invention.

EXAMPLE

Sample Preparation

100 μl of the cell lysate containing RNA virus (Human immune deficiency virus—HIV) and 500 cells of *E. coli* containing a plasmid construct (with codes according to the present Invention) is extracted using the RNeasy® Mini Kit® Qiagen. USA). The reagents of the kit are prepared according to the manufacturer's instructions and 350 μl of RLT buffer and 250 of 100% ethanol are added to 100 μl of viral lysate. The sample is transferred to a spin column and centrifuged at 8,000 ref for 30 seconds. The sample is washed on the spin column three times, once with 700 μl RW1 buffer and twice with 500 μl RPE buffer. After each wash the spin column is centrifuged at 8000 ref for 30 seconds. After washing, the column is thoroughly dried with a 1 minute centrifugation at 8,000 ref. Finally, the sample is eluted from the column by adding 50 μl RNase-free water to the column and centrifuging for 1 minute at 8,000 ref. The RNA is further concentrated by re-applying the eluate to the column and centrifuging a second time at 8,000 ref for 1 minute. RNA/NUCLEIC ACIDS concentration is determined using a spectrophotometer (Ultrospec™ 3000 UV Visible Spectrophotometer, Pharmacia Biotech, Cambridge, England).

RT-PCR or PCR

SUPERSCRIPT® One-step RT-PCR with PLATINUM® Taq kit (Invitrogen, USA) is used for Individual RT-PCR. The reaction volume is 50 μL which consists of 25 μl 2× Reaction mix, 200 nM of each primer, 1 μl RT/Platinum mix Taq and 10 μl of RNA extract. The tubes are placed in a thermocycler, GENEAMP® 2400 PCR System (Applied Biosystams, USA) and amplified according to the following thermocycling profile: 95° C./3 min (95° C./1 min, 55° C./1 min, 72° C./1 min)×35 cycles, & 70° C./10 min.

The PCR mixture was cleaned up using a PSI clone™ device (Princeton Separation, N J, USA) according to the manufacturer's Instructions.

Cycle Sequencing

Amplicons are sequenced by cycle sequencing using ABI PRISM® BIGDYE® Big Dye Terminator Cycle Sequencing Ready Reaction Kit (Applied Biosystems, USA) on a Gene-Amp 2400 thermocycler (PE Applied Biosystems, USA) using thermocycler profile Indicated above. Unincorporated dye terminators are removed using Centrisep chromatography columns (Princeton, USA). The samples are then dried, and re-suspended in 20 μl of ABI PRISM® Template Suppression Reagent. Samples are analyzed by capillary electrophoresis using the ABI PRISM® Genetic Analyzer 310. The 47 cm×5 OSμm uncoated capillary is filled with a POP-6® polymer (acrylamide/urea polymer) and heated to 50° C. 20 μl of the sequencing mixture are pipetted into a 0.2 ml microfuge tube provided by the manufacturer (Applied Blosystems, USA). Samples are drawn into the capillary by electrokinetic injection at 2 Kv for 60 to 200 seconds. The electrophoresis is carried out at 15 Kv for 20 minutes.

The sequence is then read using an electropherogram in accordance with the procedure outline above.

REFERENCES 1. van Doornum G J J, Guldemeester J, Osterhaus ADME, Niesters HGM. Diagnosing herpes virus infections by real-time amplification and rapid culture. J Gun Microbiol. 2003:41:576-580.
2. Akduman O, Ehret J M. Messina K, Ragsdale S, Judson F N Evaluation of a stand displacement amplification assay (BD ProbeTeo-SDA) for detection of *Neisseria gonorrhea* in urine specimens. Journal of Clinical Microbiology 2002:40:281-283.
3. Roth W K, Weber M, Selifried E. Feasibility and efficacy of routine PCR screening of blood donations for hepatitis C virus, hepatitis B virus, and HJV-1 in a blood-bank setting. Lancet, 1999. 353(9150):359-363.
4. Betsou F. Beaumont K, Sueur J M. Orfila J. Construction and evaluation of internal control NUCLEIC ACIDS for PCR amplification of *Chlamydia trachomatis* NUCLEIC ACIDS from urine samples. J Clip Microbial. 2003; 41: 1274-1276.
5. Dingle K E, Crook D, Jeffery K. Stable and noncompetitive RNA internal control for routine clinical diaginostic reverse transcription-FCR. J Gun Microbiol 2004:42, 1003-1011.
6. Gonzalez J M, Portillo M C, Saiz-Jimenez C. Multiple displacement amplification as a pre-polymerase chain reaction (pre to process difficult to amplify samples and low copy number sequences from natural environments. Environ Microbiol. 2005 July; 7(7):1 024
7. Abu Al-Soud W, Radstrom P. Effects of amplification facilitators on diagnostic PCR in the presence of blood, feces, and meaL J Clin Microbial. 2000 December; 38(12): 4463-70.
8. Vinayagamoorthy, T., Kirk Mulatz, Roger Hodkinson. Nucleotide sequence based multi-target identification. MultiGEN. Journal of Clinical Microbiology. July 2003.

What I claim is:

1. A method of testing for the presence of a target nucleic acid in a sample, the method comprising:
   (i) performing amplification, comprising combining the sample, a marker nucleic acid, and a forward and a reverse amplification primer, wherein:
      the forward and reverse primers are fully complementary to forward and reverse primer annealing sites on the target nucleic acid and on the marker nucleic acid,
      the target nucleic acid comprises a characteristic sequence, and
      the marker nucleic acid comprises a known unique sequence, which is different from the characteristic sequence and contains a coding sequence and a homonucleotide sequence upstream of the coding sequence, the homonucleotlde sequence comprising at least as many bases in length as the characteristic sequence,
      thereby generating a marker amplicon containing the unique sequence, and, when the target nucleic acid sequence is present in the sample, a target amplicon containing the characteristic sequence;
   (ii) performing sequencing, thereby identifying the sequence of at least part of the coding sequence and, when the target nucleic acid is present in the sample, at least part of the characteristic sequence, wherein:
      the sequencing comprises combining the amplicon or amplicons generated in step (i) and a sequencing primer that is complementary to a sequencing primer annealing site in the marker ampiicon and to a sequencing primer annealing site in the target amplicon, and
      the sequencing further comprises a detection step using an automated sequencing machine, wherein a channel for detecting a nucleotide in the homonucleotide sequence is turned off for at least a portion of the detection step;

thereby determining the presence or absence of the target nucleic acid sequence in the sample.

2. The method of claim 1, wherein the coding sequence encodes specific information according to a pre-determined artificial code, and wherein the method further comprises decoding said coding sequence by reference to said artificial predetermined code, thereby extracting the specific information.

3. The method of claim 2, wherein said coding sequence includes a plurality of clusters of bases incorporating said artificial code, separated by one or more sequences of homonucleotides acting as coding spacers.

4. The method of claim 2, wherein said sample and said marker are contained in a solution obtained from an unknown target source, and information revealed from said coding sequence is used to identify said unknown source of said solution.

5. The method of claim 1, wherein the amplification in step (i) is carried out by polymerase chain reaction.

6. The method of claim 1, wherein the sample is a first sample and the marker nucleic acid is a first marker nucleic acid and the method is used to test multiple samples and further comprises carrying out steps (i) and (ii) on one or more additional samples using the forward and reverse amplification primers, the sequencing primer, and for each additional sample, an additional marker nucleic acid, wherein each additional marker nucleic acid contains the forward and reverse amplification primer binding sites and a unique nucleotide sequence that is different from the characteristic sequence and different from the unique sequence of the first marker nucleic acid wherein detection of two or more unique marker nucleotide sequences in any sample thereby reveals cross-contamination.

7. The method of claim 1, wherein said sample is obtained from a source that may include an inhibitor of said amplification and the method further comprises determining that the amplification was not inhibited by said inhibitor, based on the sequencing of the at least part of the coding sequence.

8. The method of claim 1, wherein the characteristic sequence is a first characteristic sequence, the marker nucleic acid is a first marker nucleic acid, the forward and reverse primers are first forward and reverse amplification primers, said target nucleic acid further comprises one or more additional characteristic sequences distinct from the first characteristic sequence, and step (i) further comprises combining, in the same reaction, for each of the additional characteristic sequences: a set of additional forward and reverse amplification primers, which primers are distinct from the first forward and reverse primers and are complementary to sites flanking the additional characteristic sequence, and an additional marker, which additional marker comprises sites complementary to the additional amplification primers and an additional unique sequence that is distinct from the unique sequence in the first marker, and step (ii) further comprises sequencing at least part of each additional characteristic sequence and at least part of the unique sequence in each additional marker.

9. The method of claim 1, wherein the sequencing in step (ii) further comprises providing a polymerase, nucleotides, and chain-terminating nucleotides under conditions that permit hybridization of the sequencing primer to sequencing primer annealing sites in the marker amplicon and, when present, in the target amplicon, and extension of the sequencing primer.

10. The method of claim 1, wherein the sequencing primer annealing site in the marker amplicon and, where present, in the target amplicon, is located between the respective forward and reverse primer binding sites.

* * * * *

SEQUENCE LISTING

```
<160> NUMBER OF SEQ ID NOS: 19

<210> SEQ ID NO 1
<211> LENGTH: 42
<212> TYPE: DNA
<213> ORGANISM: Artificial
<220> FEATURE:
<223> OTHER INFORMATION: Synthetic oligonucleotide

<400> SEQUENCE: 1
atgtccttta tatatttgcg cgctttaaac cctttgggaa aa                          42

<210> SEQ ID NO 2
<211> LENGTH: 16
```

```
<212> TYPE: DNA
<213> ORGANISM: Artificial
<220> FEATURE:
<223> OTHER INFORMATION: Synthetic Oligonucleotide

<400> SEQUENCE: 2 aaacccttg ggaaaa                                                      16

<210> SEQ ID NO 3
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 3
aaacccgggt ttaaaa                                                     16

<210> SEQ ID NO 4
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 4
aaagggccct ttaaaa                                                     16

<210> SEQ ID NO 5
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 5
gggaaaccct ttaaaa                                                     16

<210> SEQ ID NO 6
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 6
aaatttcccg ggaaaa                                                     16

<210> SEQ ID NO 7
<211> LENGTH: 16
<212> TYPE: DNA
<213> ORGANISM: Artificial Sequence
<220> FEATURE:
<223> OTHER INFORMATION: Sunthetic Oligonucleotide

<400> SEQUENCE: 7
tttaaacccg ggaaaa                                                     16

<210> SEQ ID NO 8
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 8
```
cccaaatttg ggaaaa                                                  16

<210> SEQ ID NO 9
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 9
ccctttaaag ggaaaa                                                  16

<210> SEQ ID NO 10
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 10
ccctttgggc ccaaaa                                                  16

<210> SEQ ID NO 11
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 11
gggtttgggc ccaaaa                                                  16

<210> SEQ ID NO 12
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 12
gggcccaaat ttaaaa                                                  16

<210> SEQ ID NO 13
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 13
gggtttaaat ttaaaa                                                  16

<210> SEQ ID NO 14
<211> LENGTH: 88
<212> TYPE: DNA
<213> ORGANISM: Artificial Sequence
<220> FEATURE:
<223> OTHER INFORMATION: Synthetic Oligonucleotide

<400> SEQUENCE: 14
aaaaaaaaaa aaaaaaaaaa aaaaaaatgt cctttatata tttgcgcttt aaaccctttg   60
ggaaaaactt aatggtatta gattctcg                                     88

<210> SEQ ID NO 15
<211> LENGTH: 24

```
<212> TYPE: DNA
<213> ORGANISM: Artificial Sequence
<220> FEATURE:
<223> OTHER INFORMATION: Synthetic Oligonucleotide

<400> SEQUENCE: 15
tctagatcat ggctatttgg acag                                              24

<210> SEQ ID NO 16
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 16
aaaaaaaaaa aaaaaaaaaa aaaaaaaaaa tctagatcat ggctatttgg acag             54

<210> SEQ ID NO 17
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 17
tctagatgat ggctatttgg acagaaaaaa atctagatca tggctatttg gacag            55

<210> SEQ ID NO 18
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 18
tctgtctggc ttttggcgtc tgtctggctt ttggcg                                 36

<210> SEQ ID NO 19
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 19
aaaaaaaaaa aaaaaaaaaa aaaaaaaaaa tctagatcat ggctatttgg acag             54
```